United States Patent [19]

Sypal et al.

[11] Patent Number: 5,152,767
[45] Date of Patent: Oct. 6, 1992

[54] INVASIVE LITHOTRIPTER WITH FOCUSED SHOCKWAVE

[75] Inventors: Kenneth L. Sypal, Glen Ellyn; Robert M. Schildgen; Robert R. Mantell, both of Arlington Heights, all of Ill.

[73] Assignee: Northgate Technologies, Inc., Arlington Heights, Ill.

[21] Appl. No.: 617,169

[22] Filed: Nov. 23, 1990

[51] Int. Cl.⁵ .............................................. A61B 17/22
[52] U.S. Cl. .................................................... 606/128
[58] Field of Search ............................ 606/127, 128; 128/24 EL; 367/147; 313/130, 141, 268, 613

[56] References Cited

U.S. PATENT DOCUMENTS

| | | | |
|---|---|---|---|
| 3,283,294 | 11/1966 | Schrom | 367/147 |
| 4,190,051 | 2/1980 | Iglesias | 606/128 |
| 4,476,412 | 10/1984 | Nishida et al. | 313/130 |
| 4,611,594 | 9/1986 | Grayhack et al. | 606/127 |
| 4,691,705 | 9/1987 | Okada | 606/127 |
| 4,927,427 | 5/1990 | Kriauciunas et al. | 606/128 |
| 5,041,121 | 8/1991 | Wondrazek et al. | 606/128 |

FOREIGN PATENT DOCUMENTS 1218112  6/1966  Fed. Rep. of Germany ...... 606/128

Primary Examiner—Lee S. Cohen
Assistant Examiner—K. M. Pfaffle
Attorney, Agent, or Firm—Robert M. Wolters

[57] ABSTRACT

An invasive lithotripter includes a pair of electrodes having rectangular cross sections, and having flat faces of rectangular configuration confronting one another. An insulating member is interposed between the electrodes and spaces them apart a predetermined distance. The insulating member at its forward edge is relieved to provide portions of the electrode flat faces exposed and confronting one another to permit an electrical spark to jump between the exposed portions of the electrode faces. The relieved portion comprises a reflector having a focus point. The portions of the electrodes facing one another across the relieved area are provided with protuberances aligned with the focus point. A spark across the exposed portions of the faces of the electrodes in an aqueous medium generates a shockwave that is focused by the reflector. A shield surrounds and extends beyond the electrode and the insulating member to inhibit radial propagation of shockwave energy while enhancing axial propagation thereof.

10 Claims, 2 Drawing Sheets

INVASIVE LITHOTRIPTER WITH FOCUSED SHOCKWAVE

BACKGROUND OF THE INVENTION

Kidney stones and other naturally occurring stones in the urinary bladder, gall bladder, kidneys, or ureter can be exquisitely painful, and in the past have required surgical relief. Excision or destruction of stones in the bladder can often be accomplished by entrance thereto through the urethra with an endoscope for viewing, and either a retracting or fracturing tool, or a lithotripter for generating a hydraulic shockwave in the immediate vicinity of the stone or stones. Obviously, a lithotripter must be small to enter through the urethra, or through a small surgical incision into the kidney, the bladder, or the gall bladder. A shockwave is generated by a high voltage spark jumping between two closely spaced electrodes. However there has heretofore been no way of concentrating the energy directly on the stone and the energy (with the exception of that hitting the stone) generally radiates in all directions from the electrodes. This radiated energy is unwanted and can possibly perforate the surrounding tissue which can lead to many complications of an otherwise simple procedure.

OBJECTS AND SUMMARY OF THE PRESENT INVENTION

It is the principal object of the present invention to provide an invasive type lithotripter with electrodes that are smaller than those heretofore used with similar or greater power shockwave delivery than larger electrodes.

It is a further object of the present invention to provide an invasive lithotripter with means for focusing the shockwave generated by a spark jumping between two electrodes.

It is a further object of the present invention to provide an improved safe electrode wherein the tip is protected by an outer wrap which prevents hydraulic shockwave from exiting radially from the tip, and essentially permits only axial shockwaves.

The foregoing and other objects are met in the present invention by the provision in combination of a parabolic or semi-spherical reflector, with rectangular electrodes disposed axially of the reflector on opposite sides thereof. A spark is discharged between the electrodes substantially across the apex of the reflector. A protective shell surrounds the reflector and the electrode. The parabolic or semi-spherical reflector focuses the shockwave to be concentrated on the stone or stones to be disintegrated. The rectangular electrodes cooperate with the reflector in providing the spark, and hence the shockwave at the proper location. Furthermore, the rectangular electrodes present the best cross sectional area utilization for the lowest resistance per length as compared with a coaxial cable type electrode to provide the best efficiency of transferring electrical energy to the spark tip. The delivered energy is on the order of 4-8 kilovolts DC with currents ranging from 100 to 500 amperes for short durations of about 1 microsecond. As can be seen, slight decreases in resistance can substantially reduce the electrode energy losses, while delivering high energy electro-hydraulic shockwaves.

Also, rectangular electrodes permit the best spacing possible at the tip. It has been known that the hydraulic energy delivered is a strong function of the length of the spark gap. Rectangular electrodes with an insulator in a 2 French electrode (2 millimeter circumference) configuration permit a spark gap distance which is equal to or greater than a 3 French coaxial electrode (3 millimeter circumference). The reason for this is that the rectangular electrode tip presents only one insulator surface to the spark, whereas the coaxial electrode tip presents two insulator surfaces (one on each side of the central electrode), and thus the rectangular electrode can more efficiently utilize the cross sectional area available to provide the longest spark gap possible for a given electrode size. The capacitance per unit length is less for a rectangular electrode than for a coaxial electrode. With lower capacitance per unit length, a faster rise time spark may be generated, which causes a faster rise time hydraulic shock-wave with greater stone destruction power.

Those skilled in the art may note a tendency for medical practitioners to desire to use smaller instruments. These devices may be more easily inserted within patients with less potential harm. Recently, small optical scopes have been developed with internal channels of smaller diameter, typically of approximately 2.1 French construction (2.1 millimeter circumference). However, the stones remain the same size and require the same destructive power. Accordingly, it becomes a necessity for constructing lithotripsy electrodes with smaller cross sections but retaining similar or greater power delivery capability than larger previously available electrodes. Note that the previous electrode of choice has generally been 3 French (3.0 millimeter in circumference) with some sizes ranging up to 9 French.

THE DRAWINGS

The present invention will best be understood with reference to the following specification when taken in connection with the accompanying drawings wherein.

DETAILED DISCLOSURE OF THE ILLUSTRATED EMBODIMENT

Figure 1:
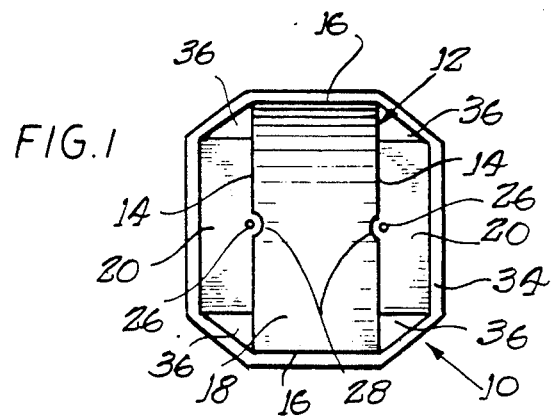
FIG. 1 is an end view of an invasive lithotripter tip constructed in accordance with the present invention.

Referring now to the figures of the drawings in greater detail, and particularly to FIGS. 1-4, there will be seen an invasive lithotripter 10 constructed in accordance with the principles of the present invention. The lithotripter includes an insulating reflector 12, which is rectangular in end view (FIG. 1), having side surfaces 14 and end surfaces 16. The insulating reflector is also rectangular in the front view of FIG. 3, with the important exception of a left facing parabolic or semi-spherical reflector surface 18. This surface is seen also in FIG. 1, where it opens toward the viewer.

Metallic, conductive electrodes 20 are disposed on opposite sides 14 of the insulating reflector 18, and are insulated from one another thereby. The outer end of each electrode 20 as indicated at 22 in FIG. 3 extends outwardly from the apex 24 of the parabolic or semi-spherical reflector 18, so that the outer portions of the electrodes are spaced from one another, and insulated from one another by the reflector 12. The ends may be struck with a punch or the like at 26 to form small protrusions 28 extending into the space above the apex of the reflector. These protrusions are located aligned with the focus of the parabolic or semi-spherical reflector. A pair of conductive wires 30 are respectively integral with or connected by any suitable means to the electrodes 20, and lead to electrical circuitry (not shown) for producing a high voltage spark between the electrodes, across the reflective surface 18. The wires 30 are individually insulated by polyamide sheaths 32, and an encapsulating polyamide sheath 34 surrounds the reflector and the electrode to hold the assembly together.

Although the initial parts of the invention have now been described, certain details thereof will be of interest. It is to be noted that the parabolic or semi-spherical reflector 18 is not a paraboloid or hemisphere of revolution, but rather is a parabolic or cylindrical section. The electrodes can be separate metallic pieces suitably secured to the conductive wires 30, or they preferably can be portions of these wires. Stainless steel may be used. Copper also presents a lower electrical resistance.

The electrode tip's important parameters include the electrode spacing, or the distance between the electrodes where the spark may jump, the protective outer wrap which provides containment and direction for the spark energy, and reflector insulator, which also provides direction for the spark energy. The primary objective is to provide the strongest spark energy in the axial direction with the weakest radial spark energy. This combination provides the safest electrode operation without fear of perforating the ureter or other tissue with the continued capability to fragment the calculi (stone).

The insulation, as noted, is preferably polyamide, which is of superior electrical characteristics, having a dielectric strength of 4,000 volts per mil. The shape of the outer insulating sheath 34 as seen in FIG. 1 is an irregular octagon. This shape provides cavities between it and the usually round lumen through which it is passed, for irrigant to flow. The rectangular electrode wires 20 provide a low capacitance per unit length, lower than an equivalent round coaxial electrode. Lower capacitance provides for faster rise times and more efficient spark generation with higher peak energies for stone disintegration.

Although it is possible for a spark to travel from one electrode surface to another electrode surface throughout the area in which the electrodes are not insulated from one another by the reflector, the projections 28 tend to localize the spark at the focus point of the reflector. Accordingly, the shockwave generated by the spark (which flashes some of the surrounding urine and any added aqueous solution into steam) is focused by the reflector so that the shockwave travels substantially linearly from the left end (as viewed in the drawings) of the lithotripter for most efficient impingement against the concretion, such as kidney stone to be disintegrated.

Figure 2:
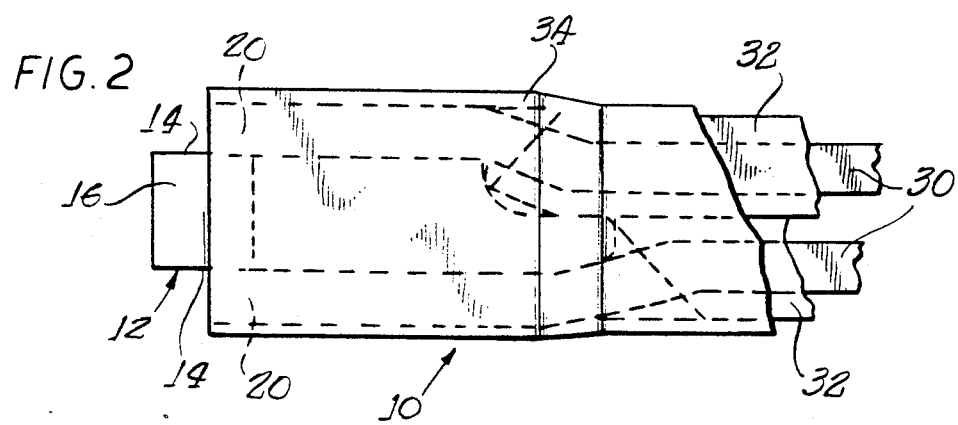
FIG. 2 is a side view of the lithotripter of FIG. 1.

The total overall dimensions are quite small. Referring first to FIG. 1, the maximum distance from left to right is 0.0212 inch, while the maximum height is 0.022 inch. The distance across diagonally opposite corners is 0.0254 inch. The electrodes 20 are 0.014 × 0.004 inch as viewed in FIG. 1. The vertical height of the reflector as viewed in FIG. 1 is 0.020 inch, while the width is 0.0112 inch. The projection of the reflector beyond the ends of the electrodes as seen in FIG. 2 is 0.005 inch, while each of the polyamide insulators 32 is 0.003 inch thick, the outer wrap 34 being 0.0005 inch thick.

The shape of the reflective surface has been set forth heretofore, and it is noted that this technically is a parabolic or semi-spherical cylinder.

Figure 5:
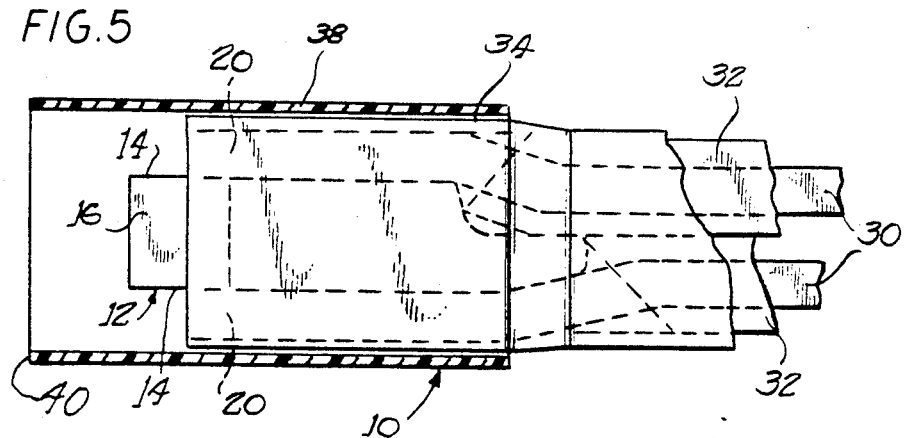
FIG. 5 is a side view partly in axial section of the lithotripter tip having a safety shield positioned around the enclosing tip and spark area.
Figure 6:
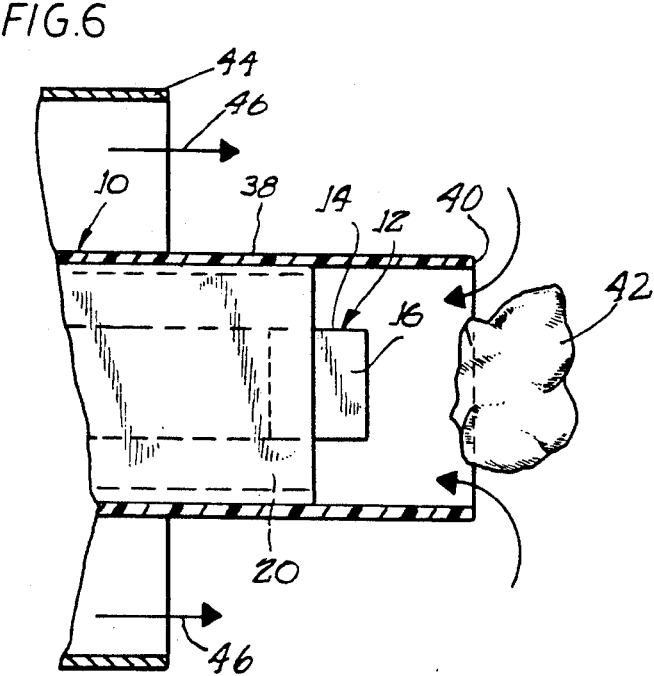
FIG. 6 is a side view partly in axial section showing the relation of the lithotripter tip to a kidney stone or other concretion.

A further important aspect of the present invention is shown in FIGS. 5 and 6. The parts heretofore described remain without change and are identified by the same numerals previously used. The distinction resides in the provision of a cylindrical shield 38 surrounding the electrodes 20 and the reflector 12. The shield 38 is made of suitable plastic material and resiliently grips the sheath 34 and extends axially beyond the reflector to a termination 40. The shield helps to locate the lithotripter 10 relative to a kidney stone 42 or the like, and helps to focus the shockwave energy on the stone. A scope 44 is shown surrounding the lithotripter in FIG. 6, and water circulation is indicated by arrows 46.

Perhaps more importantly, the shield both reflects and absorbs energy, inhibiting radial distribution of energy which might perforate surrounding tissue. Such tissue perforation would turn a simple procedure into an extensive procedure.

The present invasive lithotripter constitutes a 2 French electrode which is superior to the existing 3 French electrode that is the industry standard.

For a given transverse dimension the rectangular wires have a larger area than round wires, and thus have a lower resistance per unit length. They also have lower capacitance per unit length. The lower resistances and capacitance produce a hotter spark, and thus produce a shockwave having more energy.

The energy delivered is a strong function of the spark gap. The correct 3 French coaxial electrode has a spark gap of 0.006 inch. The spacing of the square wires in the present invention is 0.006 inch, but in the electrode area this is expanded to 0.011 inch by the insulating reflector. This increases the effective energy by a factor of about 2. This addition of the reflective surface increases the amount of energy delivered to the stone by a further factor.

Figure 3:
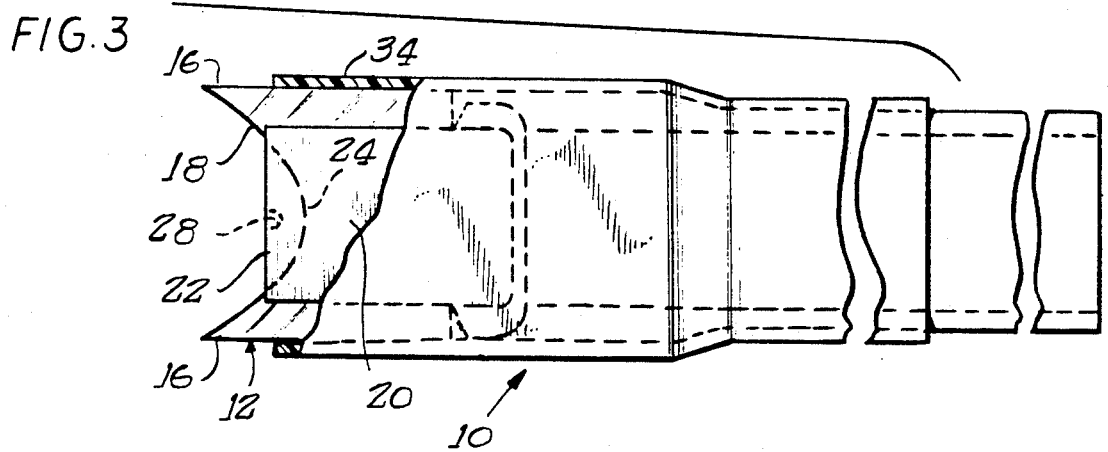
FIG. 3 is a side view taken at right angles to FIG. 2, and with a portion broken away to illustrate the electrode construction relative to the parabolic or semi-spherical reflector.
Figure 4:
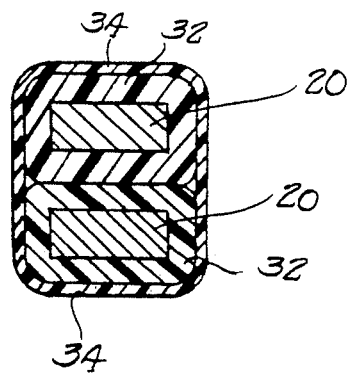
FIG. 4 is a cross sectional view of the body of the electrode showing the basic electrode construction.

In the preferred example, the electrodes 20 are simply extensions of the conducting wires 30, and the wires theretofore are of the same dimensions as the electrodes. The total length of the outer sheath 34 in FIG. 3 is 132 cm, while the total length to the right of the outer sheath is 5 cm, permitting connection to the external electronic circuitry. The protective safety shield in FIG. 5, projects approximately 2-3 mm beyond the electrode spark face dimples item 26 as in FIG. 1. The length of this extension is related to the energy applied to the electrode and the size and shape of the spark generated.

The specific example of the invention as herein shown and described is for illustrative purposes only. Various changes in structure will no doubt occur to those skilled in the art, and will be understood as forming a part of the present invention insofar as they fall within the spirit and scope of the appended claims.

The invention is claimed as follows:

1. A lithotripter comprising a pair of electrodes each having substantially rectangular cross sections and respectively having flat faces confronting one another, an insulating member of substantially rectangular cross section interposed between and spacing said electrodes a pre-determined distance apart, said insulating member having an edge opening relieved area exposing opposing portions of said electrode flat faces toward one another to permit an electric spark to jump between the exposed electrode faces, a pair of conductors respectively connected to and leading from said electrodes for conducting a spark inducing potential to said electrodes from an electrical source, a spark between said electrodes in an aqueous environment generating a shockwave to fracture a bodily concretion, and insulating material surrounding and securing said electrodes and said insulating spacing member together.

2. A lithotripter as set forth in claim 1 and further including confronting protrusions aligned with one another on the exposed portions of said flat faces for localizing a spark discharge.

3. A lithotripter as set forth in claim 2 wherein the relieved area of said insulating member provides a reflector surface for focusing the shockwave.

4. A lithotripter as set forth in claim 3 wherein the reflector surface on the insulating member has a focus point, and wherein said protrusions are aligned with said focus point.

5. A lithotripter as set forth in claim 1 wherein the relieved area of said insulating member provides a reflector surface for focusing the shockwave.

6. A lithotripter as set forth in claim 1 wherein the confronting faces of the electrodes are rectangular.

7. A lithotripter as set forth in claim 6 wherein said conductors respectively comprise extensions of said electrodes with substantially the same cross section.

8. A lithotripter as set forth in claim 1 wherein said insulating member comprises a ceramic member.

9. A lithotripter as set forth in claim 1 wherein said flat faces further have longitudinal edges and a predetermined width between said longitudinal edges, said insulating member being wider than said predetermined width and extending on both sides beyond said longitudinal edges, said insulating member extending beyond outer ends of said flat faces and being relieved behind said outer ends.

10. A lithotripter as set forth in claim 1, said insulating material including a shield surrounding and extending beyond said electrodes and said insulating member and preventing radial shockwaves and permitting axial shockwaves.

* * * * *